United States Patent [19]

Pera

[11] Patent Number: 4,775,525

[45] Date of Patent: Oct. 4, 1988

[54] ORAL HYGIENE FORMULATION CONTAINING SODIUM ALGINATE

[76] Inventor: Ivo Pera, 314 McBrien Rd., Royal Arms Apt. 5107-8, Chattanooga, Tenn. 37411

[21] Appl. No.: 809,428

[22] Filed: Dec. 16, 1985

[51] Int. Cl.[4] .......................... A61K 7/26; A61K 7/16
[52] U.S. Cl. ........................................ 424/58; 424/54; 514/779
[58] Field of Search ..................... 514/779; 424/54, 58

[56] References Cited

U.S. PATENT DOCUMENTS

| | | | |
|---|---|---|---|
| 3,122,483 | 2/1964 | Rosenthal | 167/93 |
| 3,686,393 | 8/1972 | Woodruff et al. | 424/50 |
| 3,929,987 | 12/1975 | Colodney et al. | 424/52 |
| 4,022,880 | 5/1977 | Vinson et al. | 424/50 |

OTHER PUBLICATIONS

Gershon et al., in *Cosmetics, Science and Technology*, vol. 1, Wiley-Interscience, N.Y., 1972, pp. 490-493.
Technical Bulletin DB-1—Kelgin & Kelvis Sodium Alginates by Kelco, a Division of Merck & Co., PVP Chapter 21—GAF Corp.

*Primary Examiner*—J. R. Brown
*Assistant Examiner*—F. T. Moezie
*Attorney, Agent, or Firm*—John H. Faro

[57] ABSTRACT

A dental treating composition and method are disclosed which reduces dental plaque and inhibits future formation of the same, when the dental treating composition is used on regular basis. Sodium alginate is used as a calcium ion chelating agent which weakens the bond between the plaque and the teeth thereby allowing easy removal by subsequent brushing. The use of benzalkonium chloride and zinc sulfate with the composition provides for desensitizing the teeth and elimination of halitosis.

14 Claims, No Drawings

ORAL HYGIENE FORMULATION CONTAINING SODIUM ALGINATE

BACKGROUND OF THE INVENTION

1. Field of the Invention

This invention pertains to formulations and methods for promoting oral hygiene and in particular to formulations and methods for reducing tooth decay by removing dental plaque.

2. Description of the Prior Art

The etiology of dental conditions involves complex interactions of various natural oral substances and chemical reactions between the same and dentifrices. Enough conditions exist to warrant not only a health professional, namely a dentist devoted solely to a person's teeth and gums, but also specialization within that profession. For example, periodontics, endodontics, and orthodontics are some of such areas of specialization. Notwithstanding the relatively large number of professionals devoted to the care and treatment of teeth and gums, it may safely be said that tooth decay caused by bad oral hygiene is one of the more prevalent health problems in the United States today.

Generalized factors that predispose individuals to poor oral health include endogenous (microbiological) hose (habit and custom) and exogenous (diet) aspects.

In terms of microbial concentration, the mouth is perhaps the most "dirty" organ of the body; that is, the potential for infection is greater there than elsewhere. Conditions which are present in the mouth, including an overabundance of nutrients, moisture, a warm ambient temperature, and oxygen are ideal for supporting microbial growth. Microorganisms establish colonies preferentially at various anatomical sites within a person's mouth. Moreover, no two areas of the mouth possess an identical ratio of bacterial flora (microscopic forms of life). Other variables which significantly affect floral patterns include oral pH, chewing habits, hygiene habits, time of day and age of the patient. Hence, in the prior art, no generalized treatment of the mouth exists to effectively prevent caries or related gum disease.

Brushing of the teeth, preferably after eating, is widely recognized as the fundamental method of promoting oral hygiene. Almost everyone prefers to use a commercial dentifrice to brush their teeth. These products come in toothpaste, tooth powder, and the newer dental gel forms. Their composition is fairly standard: a binder to stabilize the suspension emulsions liquid and solid phases, an abrasive to remove debris, a sudser to foam and froth the teeth clean, a humectant to retain moisture, and a flavoring agent. Other active ingredients with claimed therapeutic and/or preventative proprieties such a fluoride, may also be included within the formulations of the prior art. Powder dentifrices normally contain only abrasive and flavoring ingredients.

Studies have shown that dentifrices vary greatly in abrasiveness. In general, while no abrasive is harsh enough to remove enamel, some dentifrices may harm cementum and dentin. These products should be avoided by individuals with periodontal disease and hypersensitive teeth. Identifying the different kinds of offending dentifrices is difficult because the interaction of inert ingredients in each formula (which changes over time) may enhance or retard the effect of the abrasive within the mixture. In general, powders are more abrasive than pastes, and products that claim to be tooth whiteners often are harsher than others. Specific abrasive ingredients which may harm dentin include calcium carbonate, anhydrous dibasic calcium phosphate and silica.

Many therapeutic claims are made about the various dentifrices. However, presently only fluoride containing dentifrices appear to be helpful in preventing dental cavities. Fluoride in each of its various dosage forms partially decreases the incidence of cavities by converting hydroxyapatite in the enamel to a harder and less acid soluble fluoroapatite. Certain desensitizing toothpastes also are promoted as being therapeutically beneficial in treating teeth which are hypersensitive when they are exposed to variations in physical stimuli such as temperature and pressure. Such hypersensitiveness may be caused due to an enamel defect or early pulpitis.

There is a continuing effort in the prior art to obtain additional dental benefits from dentifrices through the inclusion of agents designed to have some specific biological or therapeutic action. Among such dentifrices are those which are claimed to "remineralize" the tooth substance, those which include urea and dibasic ammonium phosphate in their formulas, penicillin, foaming agents, and others which have been promoted as antienzyme, antibacterial and antihalitosis agents. For the most part, when such dentifrices are employed as adjuncts to supervised toothbrushing in controlled clinical investigations, their superiority over conventional dentifrices has not been clearly established.

The term halitosis has become a household word due to intensive commercial advertising. Recent television advertising has implicated bad breath as a causative factor in social insecurity. While no one doubts that bad breath can be offensive, there is some doubt as to whether mouthwash is the solution to the problem as it is advertised. While the lungs contribute a small share to the problem of bad breath, most bad breath problems arise in the mouth. Mouth odor is usually at a peak in the morning due to the combination of bacteria, decaying foodstuffs, and mouth protein, which have stagnated overnight. The involvement of bacteria is the scheme of things has led many manufacturers to include antibacterial agents, for example, quaternary ammonium compounds, tyrothricin, etc., in their products. Claims that an antibacterial can effectively kill the bacteria causing bad breath during the short duration of time of the average gargle are questionable. Secondly, the lining of the mouth is protein and the quaternary ammonium compounds used in many mouthwashes are absorbed and partially deactivated by the protein. Even if these compounds are leached out of the mouthwash by the saliva, there is no evidence to indicate that they are active over the period of a day. They also are indefinitely diluted. It would appear, therefore, that mouthwashes are primarily useful in partially rinsing away collected malodorous materials in the mouth; but, such rinsing may also be effectively accomplished by gargling with water. Some pleasant scent will also remain behind for a little while after gargling with the mouthwash. In general, however, mouthwashes are not significantly effective in eliminating halitosis, but they may mask halitosis for a limited time and cause the user to develop a false sense of security.

Dental plaque comprises a thin, sticky, transparent film that forms continuously on the surfaces of the teeth. Certain bacteria, especially those on the inner surface of the plaque, produce acids that can attack the tooth enamel. Plaque can also build up over time and harden into a complex material called dental calculus or tartar. The mixture of deposits within dental calculus can lead to gum disease and tooth loss as well as tooth cavities. Calculus generally manifests itself by the formation of hard calcified deposits which form at or beneath the edge of the gum. While tooth decay encouraged by plaque would almost be totally prevented by the elimination of plaque, no satisfactory method in the prior art has been found to avert the formulation of bacterial plaque on teeth or to effectively remove the same to prevent buildup. Neither the various dentifrices nor the mouthwashes of the prior art prevent the formation of or permit the removal of dental plaque.

Regular visits to the dentist during which the teeth are thoroughly cleaned are, of course, effective in removing the plaque then built up on the teeth. However, the period of time between such visits allows the plaque to build up and to cause the aforementioned damage.

Accordingly, a major object of the present invention is to provide a formulation which when used on a daily basis, prevents the buildup of dental calculus.

Another object of the present invention is to provide dentifrice composition containing a combination of several active substances which provide special, effective dental care, solving jointly most of the problems of the mouth such as hypersensitivity, halitosis, and plaque.

Another object of the present invention is to provide a dentifrice composition which is foamless and may therefore be used by persons without the need to rinse their mouths after each use.

A related object of the present invention is to develop a dentifrice and method which is effective and yet not taste repugnant to the user.

There are also other objects of the present invention which although may not be specifically stated, may be deduced from the following description and claims and which other objects are intended to be included within the scope of the present invention.

SUMMARY OF THE INVENTION

The present invention accomplishes the above-stated objects as well as others by providing an ingestible toothpaste which when used on a daily basis, is primarily intended to remove dental plaque and secondarily intended to reduce hypersensitivity, and halitosis. Incident to such accomplishments, the dentifrice provided herein thereby reduces oral caries, prevents gum diseases, and otherwise promotes good, effective oral hygiene.

The essential active ingredient of the present invention is a calcium ion chelating agent comprising sodium alginate. The removal of calcium ions weakens plaque so that it may be easily removed by brushing or other mild forms of abrading actions. The following functional agents are also included within the inventive dentifrice: antimicrobiological agent, antihalitosis agent, binder, desensitizing agent, fluoride, humectant, coloring agent, flavoring agent, and a sweetener. The binder functions as a hydrocolloidal agent which thickens the mixture and provides an aesthetically appealing texture to the formulation. Benzalkonium chloride comprises the antimicrobacterial agent; strontium chloride comprises the desensitizing agent; and, zinc sulfate comprises the antihalitosis agent. The humectant is used to retain moisture within the formulation when it is exposed to the air in order to prevent the paste from hardening.

DESCRIPTION OF THE PREFERRED EMBODIMENTS

The development of plaque on a person's teeth is influenced by endogenous and exogenous factors. Dental plaque is a soft, deposit that tenaciously adheres to dental surfaces. It is composed of bacteria and salivary byproducts such as protein, mucin, and colloidal materials. Plaque begins as a thin invisible and insoluble film which traps more and other materials and bacteria. Food residue after meals can be incorporated into plaque by bacterial degradation and conversion into dextran and glycoproteins. Left unchecked, the plaque thickens and bacteria proliferate. Eventually, plaque around the base of the crown calcifies by calcium salt precipitation from the saliva. Such plaque is commonly recognized as the source of microbes that cause caries and periodontitis. Plaque buildup is, therefore, related to the incidence of oral disease, whether of the tooth, its root, the bone structure, or the germs.

Foods with a high concentration of refined sugar (sucrose) are strongly cariogenic. Sucrose is converted by bacterial plaque into volatile acids such as lactic pyruvic, acetic, propionic, and butyric acid which attack, dissolve and solublize the calcium salt in the structure of teeth.

Because caries and periodontal disease are caused chiefly by destruction of vulnerable tissues by microbial byproduct formation, preventive dental techniques should be oriented toward ridding the mouth of plaque and destroying disease producing pathogens. The dentifrice described herein accomplishes these goals.

As previously stated above, an ingredient of the formulation provided herein comprises sodium alginate. Sodium alginate is effective as a calcium ion chelating agent. The sodium alginate provides removal activity against calculus and plaque on a tooth surface. The sodium alginate functions to remove calcium ions from the plaque which thereby weakens the plaque so that it can be easily removed thereafter by normal brushing or other mild abrading actions, such as rubbing the teeth with a finger or even a person's tongue. Once the plaque is removed, continued use of the dentifrice formulation prevents future plaque buildup. Since sodium alginate derives from seaweed, it is ingestible and non-toxic. These characteristics greatly enhance the use of the dentifrice under conditions where prior art dentifrices were either unable to be used or inconvenient to use. These latter uses comprise use by the young, the old, the infirmed and where wash basins and/or water are unavailable.

Testing in a typical family setting under normal living conditions has shown that the stated results are achieved when the suggested formulation is used as a toothpaste. Dental plaque was substantially eliminated and did not reform after only six months of use. Halitosis was significantly reduced; both gum and teeth sensitivity were also reduced. Concentrations of from 1% to 20% by weight of sodium alginate were used in the tests. The lower level of concentration proved to be effective but not as effective as the higher level of concentration. Taste and texture tended to be adversely affected by the higher levels of concentration. Therefore, while effectiveness is not diminished, public acceptance may be diminished by high levels of concentration of sodium alginate. The testing involved participants varying in age from six years to sixty years. Mouth feel, ingestibility and effectiveness were evaluated. As a result of the testing, is has been determined that a concentration of 7% of sodium alginate was preferred.

Benzalkonium chloride, a rapidly acting non-irritating cationic surface active agent, is a useful, all purpose, local antibacterial agent for application to skin tissues and mucous. In the dentifrice formulation provided herein, it is used for its germicidal action. Benzalkonium chloride in the range of 0.05% to 3% by weight may be used in the dentifrice formulation. Solutions of benzalkonium chloride have low surface tension and possess detergent and emulsifying properties that aid the penetration and wetting of tissue surfaces. Like other cationic surface active agents, it has certain limitations. It cannot be relied upon to kill clostridial spores; it is inactivated by soap and other anionic surface active agents; and, when applied to the skin it has a tendency to form a film under which bacteria remain viable. It is, however, a good disinfectant for wounds, burns, and other similar conditions and does kill many pathogenic nonsporulating bacteria and fungi.

Zinc sulfate is used in the formulation to overcome halitosis. The quantity used in the formulation is well below the amount which would be used in an emetic formulation. its antiseptic properties further serve, in the disclosed formulation, to treat minor disorders within the mouth and gums.

Strontium chloride derives from strontium carbonate fused with calcium chloride, the melt being extracted with water and the solution being concentrated and crystallized. In the formulation comprising the dentifrice, the strontium chloride provides a convenient, rapid, non-toxic, therapeutic method for the daily treatment in the control of painful dentin commonly known as hypersensitive dentin. The strontium chloride in accordance with its water soluble ability, functions to release strontium ions from the toothpaste during normal brushing procedures. When applied to surfaces of teeth, the strontium ions are adsorbed on the edontoblastic fibrils or in the dentinal tubules thus blocking the transmission of neural impulses from the dentinal surface to the dental pulp. Strontium chloride may be used between the range of 0.1% to 3% by weight in the dentifrice formulation.

An appropriate sweetener such as saccharin, or nutrasweet in the range of 0.1% to 1% by weight may be used in the dentifrice formulation in order or provide an appropriate sweet taste. Also, the inventive formulation may be made in a large variety of flavors and colors between the range of 0.1% to 5% by weight to satisfy any taste predilection. For example, flavors may comprise orange, lemon, cherry, strawberry, vanilla, chocolate, etc.; while appropriate colors may include orange, yellow, red, pink, green, etc. Finally, a binder may be used with the formulation in order to achieve acceptable colloidal and thickness properties. Polyvinylpyrrolidone between the range of 1% to 15% by weight may be used for these purposes. Polyvinylpyrrolidone is a synthetic polymer comprising mainly linear 1-vinyl-2-pyrrolidone groups. It is a white, free flowing amorphous powder, soluble in water and organic solvents. It is a polyamide that possesses good complexing and colloidal properties and is physiologically inert. It is used in a wide variety of applications, each based on its outstanding solution properties and film forming and adhesive qualities. Within the toothpaste formulation described herein, polyvinylpyrrolidone may be used as a hydrocolloidal to finely dispense the other active ingredients and as a binder to achieve an acceptable or palatable mouth feel. It may also be used for its thickening ability thereby providing an aesthetically appealing texture to the formulation.

It is to be noted that all of the above substances, when formulated in accordance with the range suggested or in accordance with the representative example shown hereinafter, are ingestible. That is, there is no need or requirement to rinse the mouth of the dentifrice after it has been used. Such dentifrice is therefore further useful as a toothpaste for children, travelers, the aged in nursing homes, and for hospital use in the maintenance of oral hygiene for physically or mentally handicapped patients. Furthermore, the new ingestible dentifrice may be made non-sudsing or foamless. In this way, the dentifrice does not rely upon the frothing action of the formulation to cleanse the teeth as does prior art formulations. The lack of sudsing or producing a foam is particularly important in resolving a problem among hospital and nursing care patients who on occasion choke on the air bubbles within the prior art foaming type of toothpaste. The ingestible formulation also confers benefits upon certain categories of patients, such as those bed confined in hospitals, who might not have facilities for expectoration, paraplegics confined to wheelchairs, patients with oral facial paralysis whose ability to expectorate is limited, the mentally handicapped and others whose illness requires that an attendant carry out the toothbrushing for them. The fact that the inventive toothpaste does not require for its use, enhances its usefulness for those patients and conditions mentioned above.

In use, any of the exemplary dentifrices may be utilized by applying it with an ordinary toothbrush or by applying to the teeth and gums as with a person's fingers. In the former event, the plaque, which is weakened by the chelating action of the sodium alginate, is removed by the brushing action of the toothbrush. In the latter event, the weakened plaque is removed by a person's normal functions such as eating, chewing gum or rubbing the teeth with the person's tongue or fingers. In these later circumstances, the weakened plaque is removed by the abrading action of the described functions.

Continued daily use of the exemplary dentifrices prevents the formation of new plaque due to the removal of the calcium ions so that a bond can never be formed on the teeth.

Other important functional aspects of the inventive formulation comprise the germicidal action due to the benzalkonium chloride, the desensitizing action due to the strontium chloride, and the inhibiting of halitosis due to the zinc sulfate.

The plaque removal and preventative properties of the sodium alginate is not necessarily limited to a toothpaste formulation. For example, it may be incorporated in any preparation which may be taken into the mouth such as chewing gum, a food, a beverage, or a high-velocity jet stream of water used to clean the teeth.

The following technical description and composition of the active ingredients of the disclosed formulation is presented to allow for the various compositions of the formulation and to retain the proper efficiency and quality of the preparations.

Magnesium Carbonate: Anhydrous mol. wt. 84.31, hydrated Magnesium Carbonate contains the equivalent of not less than 40.0% and not more than 43.5% of magnesium oxide (MgO). USP monograph [39409-82-0].

Benzalkonium Chloride: Solution contains not less than 95.0% and not more than 105.% of the labeled amount of benzalkonium chloride in concentrations of 1.0% or more; and not les than 93.0% and not more than 107.0% of the labeled amount in concentrations of less than 1.0% NF monograph.

Zinc Sulphate: Mol. wt. 287.54. Zinc Sulphate contains not less than 55.6% and not more than 61.0% of $ZnSO_4$ corresponding to not less than 99.0% and not more than 108.7% of the hydrated salt. USP monograph.

Sodium Fluoride: Mol. wt. 41.99. Sodium Fluoride contains not less than 98.0% and not more than 102.0% NaF calculated on a dry basis. USP monograph [7680-49-4].

Polyvinylpyrrolidone (PVP): Povidone $(C_6H_9NO)_n$ is a synthetic polymer consisting essentially of linear 1-vinyl-2-pyrrolidinone groups, the degree of polymerization of which results in polymers of various molecular weights. Mol. wts. of 10,000–95,000 may be used. USP monograph [9003-39-8].

Flavoring: Any USP listed flavoring agent can be used to suit the taste requirements desired. Listed on page 1491 of the 1985 USP, i.e., Spearment flavoring made from the following plant. Menthaspicata Linne, Menta viridis Linne. The oil contains not less than 55.0% by volume of carvone ($C_{10}H_{14}O$). NF monograph.

Sweetner: Any USP listed sweetening agent as shown on page 1492 of the 1985 USP, for example, Nutrasweet (Aspartame) contains not less than 98.0% ant not more than 102.0% of $C_{14}H_{18}N_2O_5$. NF monograph.

Strontium Chloride: $SrCl_26H_2O$. MOL. WT. 266.64. Sr 32.86%. d 1.93. mp 61°.

Coloring Agent: Any color agent may be used to suit the desires of the individual requirements as needed. USP and F D & C approved colors may be used.

Water: Quantity sufficient USP grade quality water to be used.

Glycerol: $C_3H_8O_3$. Mol. wt. 92.09. Sp gr not less than 1.249. 95.0–101.0% as glycerol. USP monograph [56-81-51].

Sodium Alginate: The purified carbohydrate product from the brown seaweeds by the use of dilute alkali. It consists chiefly of the sodium salt of Alginic Acid, a polyuronic acid composed of beta-D-mannuronic acid residues linked so that the carboxyyl groups of each unit is free while the aldehyde group is shielded by a glycosidic linkage. It contains not less than 90.8% and not more than 106.0% of sodium alginate of average equivalent weight 222.00, calculated on the dried basis. NF monograph [9005-38-3].

Representative examples of the invention, are:

EXAMPLE I

| Toothpaste: | | |
|---|---|---|
| A. Magnesium Carbonate | Approx. 3.0% | by weight |
| Benzalkonium Chloride | 0.1% | by weight |
| Zinc Sulfate | 0.4% | by weight |
| Sodium Fluoride | 0.1% | by weight |
| PVP (Polyvinylpyrrolidone) | 7.0% | by weight |
| Spearmint | 1.0% | by weight |
| Nutrasweet | 0.2% | by weight |
| Strontium Chloride | 1.0% | by weight |
| Coloring Agents | 0.2% | by weight |
| Water | 50.0% | by weight |
| B. Glycerol | 30.0% | by weight |
| Sodium Alginate | 7.0% | by weight |
| | 100.0% | TOTAL |

The glycerol and sodium alginate were prepared and mixed separately from the other ingredients. The other ingredients listed under letter "A" were then mixed with water and later added to the mixture comprising glycerol and sodium alginate (under letter "B") and then thoroughly blended to obtain a smooth texture and proper viscosity. This formulation was used in the normal manner on a toothbrush.

EXAMPLE II

Toothpaste:

Accepted formulations of the kind to be found in textbooks or on the market are supplemented with sodium alginate in the amount of 7.0% by weight of the total formulation. This is to be used in the normal manner on a toothbrush or applied to the teeth and gums as with the fingers.

EXAMPLE III

Chewing Gum:

Accepted formulations of the kind to be found in textbooks or on the market are supplemented with sodium alginate in the amount of 7.0% by weight of the total weight of the formulation. The resulting product is to be chewed in the usual manner.

EXAMPLE IV

Mouthwash:

Accepted formulations of the kind to be found in textbooks or on the market, are supplemented with sodium alginate in the amount of 7% by weight of the total weight of the formulation. The resulting product is to be used to wash the mouth by gargling.

EXAMPLE V

Lozenge Tablet:

Accepted formulations of the kind to be found in textbooks or on the market are supplemented with sodium alginate in the amount of 7% by weight of the total weight of the formulation. The resulting product is to be dissolved in the mouth in the usual manner.

EXAMPLE VI

Candy:

Accepted formulations of the kind to be found in textbooks or on the market are supplemented with sodium alginate in the amount of 7% by weight of the total weight of the formulation. The resulting product is to be dissolved in the mouth in the usual manner.

It is to be noted that the above examples are representative examples prepared in accordance with the teachings and disclosure of the specification and are not intended to be all inclusive or limiting as to the scope of the use of the present invention. For example, the sodium alginate may be used in foods, candies, mouth wash, or any other product which may be taken into the mouth or ingested by the user.

While the invention has been described, disclosed, illustrated and shown in certain terms or certain embodiments or modifications which is has assumed in practice, the scope of the invention is not intended to be nor should it be deemed to be limited thereby and such other modifications or embodiments as may be suggested by the teachings herein are particularly reserved especially as they fall within the breadth and scope of the claims here appended.

I claim as my invention:

1. An ingestible formulation which, when used on a daily basis, is effective in the prevention of the buildup of plaque and calculus upon dentition, said formulation consisting essentially of:
   (a) a plaque prevention effective amount of sodium alginate, the relative concentration of said alginate in the formulation being effective, on a daily basis, to weaken the plaque so as to permit its removal from dentition by mild abrading action; and
   (b) an ingestible binder consisting essentially of polyvinylpyrrolidone.

2. The composition of claim 1, wherein the sodium alginate is within the range of 1% to 20% by weight of the total weight of the composition.

3. The composition of claim 1, wherein the sodium alginate comprises approximately 7% of the total weight of the composition.

4. The composition of claim 1, including benzalkonium chloride within the range of 0.05% to 3.0% by weight of the total weight of the composition.

5. The composition of claim 1, including benzalkonium chloride comprising approximately 0.1% of the total weight of the composition.

6. The composition of claim 1, including zinc sulfate within the range of 0.1% to 2.0% by weight of the total weight of the composition.

7. The composition of claim 1, including zinc sulfate comprising approximately 0.4% of the total weight of the composition.

8. The composition of claim 1, including strontium chloride within the range of 0.1% to 3.0% by weight of the total weight of the composition.

9. The composition of claim 1, including strontium chloride in the amount of approximately 1% by weight of the total weight of the composition.

10. The composition of claim 1, including polyvinylpyrrolidone within the range of 1.0% to 15.0% by weight of the total weight of the composition.

11. The composition of claim 1, including polyvinylpyrrolidone in the amount of approximately 7% by weight of the total weight of the composition.

12. A method for reducing and inhibiting the formation of plaque and calculus upon dentition, said method comprising:
    (a) contacting said dentition with a dentifrice formulation consisting essentially of a plaque prevention effective amount of sodium alginate dispersed in an ingestible binder consisting essentially of polyvinylpyrrolidone, the relative concentration of said alginate in the formulation being effective, on a daily basis, to weaken the plaque so as to permit its removal from dentition by mild abrading action; and
    (b) mildly abrading said dentition concurrent with or subsequent to contact with the dentifrice formulation.

13. The method of claim 12, including the step of formulating the calcium ion chelating agent by combining sodium alginate with a dental treating carrier.

14. The method of claim 13, including the step of brushing the teeth to apply the abrading action.

* * * * *